(12) United States Patent
Choi

(10) Patent No.: US 11,116,327 B2
(45) Date of Patent: Sep. 14, 2021

(54) REGIMEN MATTRESS

(71) Applicant: Inno-Sports Co., Ltd, Xiamen (CN)

(72) Inventor: Kwan Jun Choi, Xiamen (CN)

(73) Assignee: Inno-Sports Co., Ltd, Xiamen (CN)

( * ) Notice: Subject to any disclaimer, the term of this patent is extended or adjusted under 35 U.S.C. 154(b) by 182 days.

(21) Appl. No.: 15/913,895

(22) Filed: Mar. 6, 2018

(65) Prior Publication Data
US 2019/0269254 A1    Sep. 5, 2019

(30) Foreign Application Priority Data

Mar. 1, 2018  (CN) .......................... 201820288749.4

(51) Int. Cl.
| | |
|---|---|
| *A47C 31/00* | (2006.01) |
| *A47C 27/14* | (2006.01) |
| *A47C 31/10* | (2006.01) |
| *A47C 21/04* | (2006.01) |
| *A61M 21/02* | (2006.01) |
| *A61K 36/82* | (2006.01) |
| *A61K 36/738* | (2006.01) |
| *A61K 36/63* | (2006.01) |
| *A61K 36/898* | (2006.01) |
| *A61K 36/886* | (2006.01) |
| *A61K 9/00* | (2006.01) |

(Continued)

(52) U.S. Cl.
CPC .......... *A47C 31/005* (2013.01); *A47C 21/046* (2013.01); *A47C 21/048* (2013.01); *A47C 27/148* (2013.01); *A47C 27/15* (2013.01); *A47C 31/001* (2013.01); *A47C 31/105* (2013.01); *A61K 9/007* (2013.01); *A61K 36/63* (2013.01); *A61K 36/738* (2013.01); *A61K 36/82* (2013.01); *A61K 36/886* (2013.01); *A61K 36/898* (2013.01); *A61M 21/02* (2013.01); *A61M 2021/0016* (2013.01)

(58) Field of Classification Search
None
See application file for complete search history.

(56) References Cited

U.S. PATENT DOCUMENTS

| | | | | |
|---|---|---|---|---|
| 9,775,444 | B2 * | 10/2017 | Oh ......................... | A47C 27/14 |
| 2005/0193497 | A1 * | 9/2005 | Baker ................... | A47C 27/148 |
| | | | | 5/721 |

(Continued)

FOREIGN PATENT DOCUMENTS

CN           2805531 Y    *   8/2006

OTHER PUBLICATIONS

Anthea Levi, Which Teas are the Healthiest?, Sep. 7, 2017, p. 1-6 (Year: 2017).*

(Continued)

*Primary Examiner* — David R Hare
*Assistant Examiner* — Adam C Ortiz
(74) *Attorney, Agent, or Firm* — Bayramoglu Law Offices LLC

(57) ABSTRACT

The present disclosure relates to a regimen mattress. The regimen mattress includes a memory foam, a high density (HD) foam below the memory foam, and a cover covering the memory foam and the HD foam together to form the entire mattress. The HD foam contains functional additives. The regimen mattress effectively improves the user's health condition through adding functional additives into the foam layer that is far away from the user.

22 Claims, 7 Drawing Sheets

(51) Int. Cl.
*A47C 27/15* (2006.01)
*A61M 21/00* (2006.01)

(56) References Cited

U.S. PATENT DOCUMENTS

| | | | | |
|---|---|---|---|---|
| 2007/0251017 | A1* | 11/2007 | Speer | A47C 31/001 5/737 |
| 2009/0144900 | A1* | 6/2009 | Marrache | A47C 27/005 5/484 |
| 2014/0068868 | A1* | 3/2014 | Morzano | A47G 9/00 5/691 |
| 2015/0071978 | A1* | 3/2015 | Chang | A61N 2/06 424/402 |
| 2015/0296994 | A1* | 10/2015 | Mikkelsen | A47C 21/046 5/655.4 |
| 2017/0156508 | A1* | 6/2017 | Segal | A47C 27/001 |

OTHER PUBLICATIONS

Ritesh Tiwari, Global and China Polyurethane Industry Chain (MDI, TDI & PPG) Report 2014-2017, 2017, China Market Research Reports p. 1-3 (Year: 2017).*

Zeinab S. Abdel-Rehim, M. M. Saad, M. El-Shakankery and I. Hanafy, Textile Fabrics as thermal insulators, AUTEX Research Journal, vol. 6, No. 3, Sep. 2006 p. 148-161 (Year: 2006).*

* cited by examiner

REGIMEN MATTRESS

CROSS REFERENCE TO RELATED APPLICATIONS

This application is based upon and claims priority to Chinese Patent Application No. 201820288749.4, filed on Mar. 1, 2018, the entire contents of which are incorporated herein by reference.

TECHNICAL FIELD

The present invention relates to the technical field of mattress, particularly to a regimen mattress.

BACKGROUND OF THE INVENTION

With the improvement of people's living standards, more and more people are becoming health-conscious. However, people having lifestyle diseases, such as cervical spondylosis, periarthritis, anhypnia, irradiation sickness, diabetes, adiposis, among others, may feel quite uncomfortable based on the stage of illness. Many health care products are offered to help people having different diseases mentioned above. Mattress, as an indispensable necessity, is something that people have contacted with in daily life. In order to meet the current market demands, functional design of mattresses became more important. Traditional mattresses generally consist of two layers or three layers with a simple structure and a single function for sleeping. These mattresses hardly provides the environment to alleviate the symptoms of life disease mentioned above. Therefore, it's necessary to develop a mattress with function that can effectively alleviate the symptoms of the lifestyle diseases and contribute to a healthy life style.

SUMMARY

The present disclosure provides a regimen mattress to solve the shortcomings of the prior art.

In order to achieve the above object of the invention, the following technical solution is used.

The present invention provides a regimen mattress, the regimen mattress includes a memory foam, a high density (HD) foam below the memory foam, and a cover covering the memory foam and the HD foam together to form the entire mattress. The HD foam contains a functional additive. The functional additive is any matter that can alleviate the symptoms of lifestyle diseases.

Further, the HD foam is made of 2,4-tolylene diisocyanate (TDI) and poly propylene glycol (PPG), the memory foam is made of diphenyl-methane-diisocyanate (MDI) and poly propylene glycol (PPG). Other combinations of materials can be used as well.

Further, the HD foam is a PU (Polyurethan) foam, the HD foam further comprises a soft layer and a supporting layer disposed below the soft layer.

Further, the density of the supporting layer is greater than that of the soft layer. Further, the soft layer and the supporting layer have a density ranging from 20D to 30D.

Further, the soft layer has a density ranging from 25D to 28D, the supporting layer has a density ranging from 27D to 30D.

Further, the functional additive is a tea additive or a flower additive.

Further, the tea additive is one or more selected from the group of green tea, black tea or white tea.

Further, the flower additive is one or more selected from the group of rose, jasmine, Gardenia, lilac, orchid, aloe or Camellia.

Further, the cover includes an inner cover and an outer cover.

Further, the inner cover is a material selected from the group of fire retardant material or absorbing material.

Further, the outer cover is a material selected from the group of waterproof breathable material, heat conduction material or friction heating material.

Further, the inner cover and the outer cover are detachable.

The present invention further provides a regimen mattress, the regimen mattress includes a memory foam, a high density (HD) foam below the memory foam, and a cover covering the memory foam and the HD foam together to form the entire mattress. The memory foam contains a first functional additive. The first functional additive is any matter that has the effects of degerming and deodorization.

Further, the HD foam contains a second functional additive.

Further, the memory foam is made of diphenyl-methane-diisocyanate (MDI) and poly propylene glycol (PPG), the HD foam is made of 2,4-tolylene diisocyanate (TDI) and poly propylene glycol (PPG). Other combinations of materials can be used as well.

Further, the density of the memory foam is greater than that of the HD foam.

Further, the memory foam has a density ranging from 40D to 60D, more preferably, the memory foam has a density ranging from 40D to 42D.

Further, the first functional additive is a tea additive or a flower additive. Further, the tea additive is one or more selected from the group of black tea or white tea.

Further, the flower additive is one or more selected from the group of rose, jasmine, Gardenia, lilac, orchid, aloe or Camellia.

Further, the second functional additive is a tea additive or a flower additive. Further, the tea additive is one or more selected from the group of green tea, black tea or white tea.

Further, the flower additive is one or more selected from the group of rose, jasmine, Gardenia, lilac, orchid, aloe or Camellia.

Compared with the prior art, the advantages of the present invention are as follows. Regimen mattress, can effectively improve the user's health condition through adding functional additives into the foam layer that is far away from the user. In particularly, it plays an important role in alleviating the lifestyle disease like anhypnia. The usage of tea additives or flower additives with pharmacological effects can greatly improve the user's resting environment. Besides, the additives are added in the foam layer far away from the user rather than the layer closer to the user that bacteria tends to grow due to the heat and perspiration absorbed from the user, which can avoid the efficiency losing of the additives and ensure a long-time work, thus prolonging the service life of the functional regimen mattress.

BRIEF DESCRIPTION OF THE DRAWINGS

FIG. 2-1 is a schematic diagram of the HD foam according to a first embodiment of the invention with tea additives in the soft layer.

FIG. 2-2 is a schematic diagram of the HD foam according to a first embodiment of the invention with flower additives in the soft layer.

FIG. 3-1 is a schematic diagram of the HD foam according to a second embodiment of the invention with tea additives in the supporting layer.

FIG. 3-2 is a schematic diagram of the HD foam according to a second embodiment of the invention with flower additives in the supporting layer.

FIG. 12-1 is a schematic diagram of the HD foam according to an eleventh embodiment of the invention with tea additives.

FIG. 12-2 is a schematic diagram of the HD foam according to an eleventh embodiment of the invention with flower additives.

FIG. 14-1 is a schematic diagram of the HD foam according to a thirteenth embodiment of the invention with tea additives.

FIG. 14-2 is a schematic diagram of the HD foam according to a thirteenth embodiment of the invention with flower additives.

DETAILED DESCRIPTION

The present disclosure will be further described below in detail with reference to the accompanying drawings and embodiments. However, it should be clear that the specific embodiments described herein are used only to explain the present invention, and are not intended to limit the scope of the invention.

Figure 1:
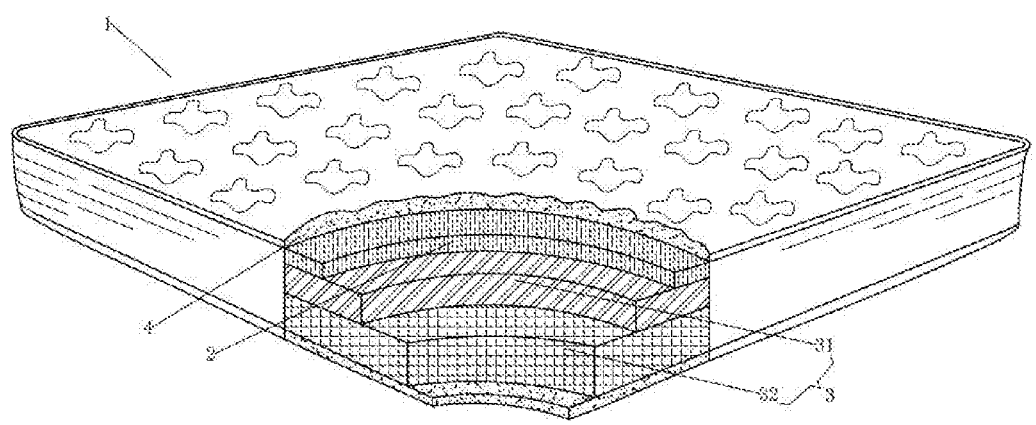
FIG. 1 is a schematic diagram of a regimen mattress of the present invention.

Referring to FIG. 1, a schematic diagram of a regimen mattress of the present invention is shown. The regimen mattress 1 includes the memory foam 2, the high density (HD) foam 3 below the memory foam 2, and the cover 4 covering the memory foam 2 and the HD foam 3 together to form the entire mattress 1. The HD foam 3 contains functional additive. The functional additive is any matter that can alleviate the symptoms of lifestyle diseases.

The HD foam 3 further includes the soft layer 31 and the supporting layer 32 disposed below the soft layer 31. The soft layer 31 is disposed, which not only enhances the comfortable feeling, making the user feel the mattress being softer, but also functions as a vibration absorber, reducing impulse when the user lies down. Soft layer 31 protects the supporting layer 32.

The HD foam 3 is made of 2,4-tolylene diisocyanate (TDI) and poly propylene glycol (PPG), the memory foam 2 is made of diphenyl-methane-diisocyanate (MDI) and poly propylene glycol (PPG). Other combinations of materials can be used as well.

Preferably, the density of the supporting layer 32 is greater than that of the soft layer 31. The soft layer 31 and the supporting layer 32 have a density ranging from 20D to 30D. More preferably, the soft layer 31 has a density ranging from 25D to 28D, and the supporting layer 32 has a density ranging from 27D to 30D.

For all the embodiments that described below, the regimen mattress 1 described above includes the memory foam 2, the high density (HD) foam 3 below the memory foam 2, and the cover 4 covering the memory foam 2 and the HD foam 3 together to form the entire mattress 1. The HD foam 3 contains functional additive. The functional additive is any matter that can alleviate the symptoms of lifestyle diseases. In the following embodiments, other elements of the regimen mattress 1 are not repeated and shown in different figures, but only details of the HD foam 3 have been described to show the different application of additives, however each and every mattress in the following embodiments include memory foam 2, cover 4, and HD foam 3. Only HD foam 3 details are given since the memory foam 2 and cover 4 are the same for each embodiment.

Figures 1, 2:
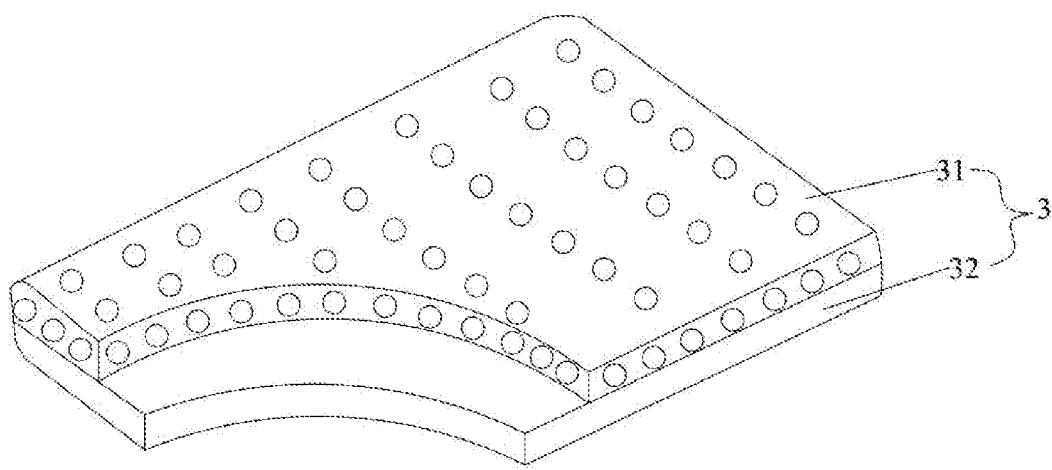
Figure 2:
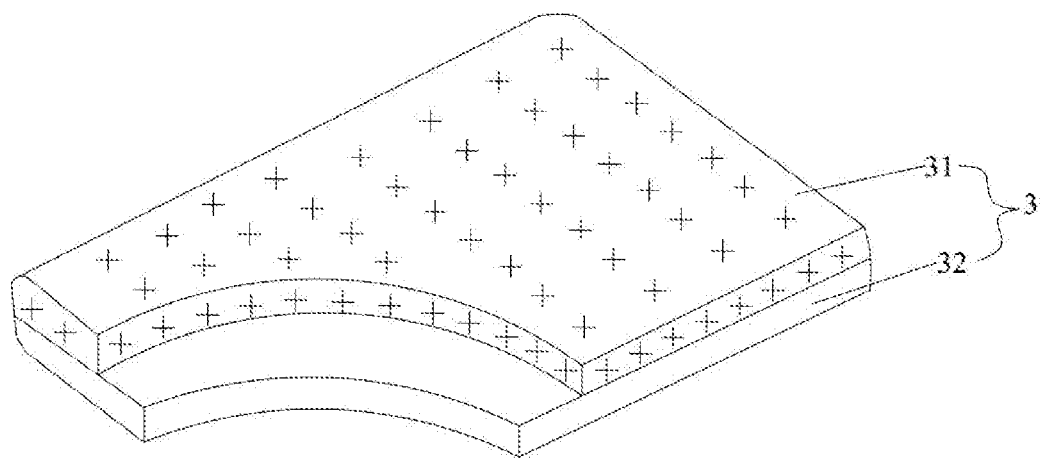

Referring to FIG. 2-1 and FIG. 2-2, schematic diagrams of the HD foam according to the first embodiment of present invention respectively with tea additives and flower additives in the soft layer are shown. The tea additives 5 is distributed in the soft layer 31 without any matter added in the supporting layer 32 is shown in FIG. 2-1 and the flower additives 6 are distributed in the soft layer 31 without any matter added in the supporting layer 32 is shown in FIG. 2-2. The distribution of tea additives 5 or flower additives 6 can be in any manner i.e. evenly or not evenly. The tea additives or the flower additives in the softer layer 31 will last longer than if they are added in the memory foam. This is because memory foam is closer to the user and that bacteria tends to grow in memory foam due to the heat and perspiration absorbed from the user. The combination of heat and perspiration would have a negative effect on the tea additives or the flower additives. Tea additives or flower additives in the softer layer 31 will have longer life time than tea additives or flower additives in the memory foam thus prolonging the service life of the regimen mattress.

Figures 1, 3:
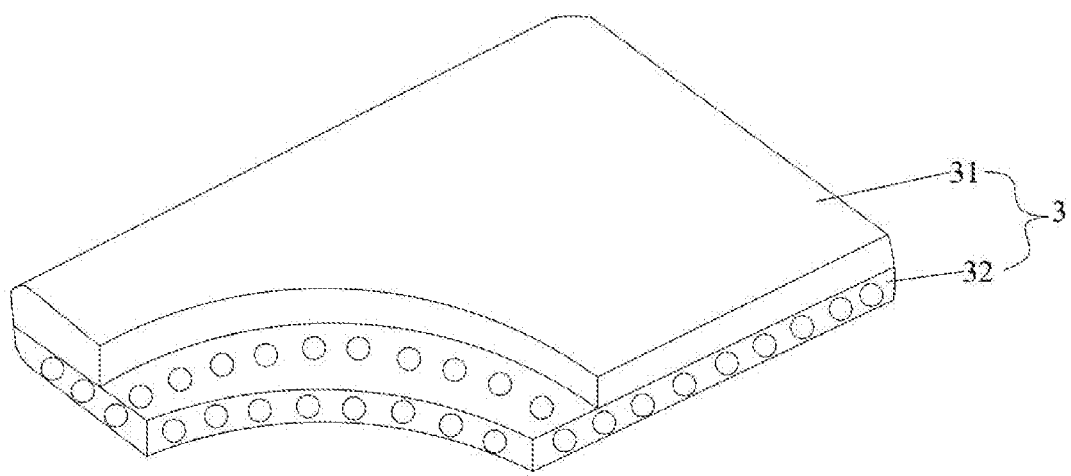
Figures 2, 3:
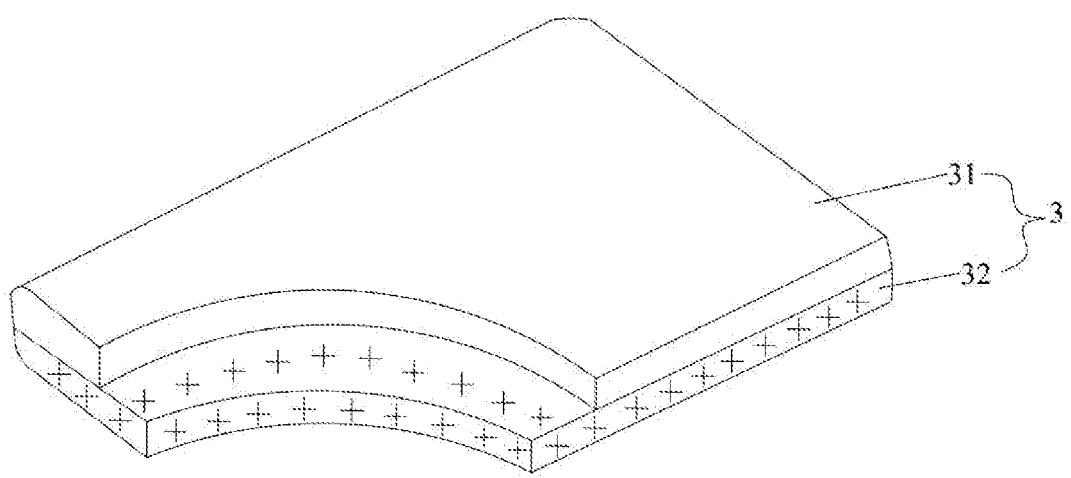

Referring to FIG. 3-1 and FIG. 3-2, schematic diagrams of the HD foam according to the second embodiment of present invention respectively with tea additives and flower additives in the supporting layer are shown. The tea additives 5 is distributed in the supporting layer 32 without any matter added in the soft layer 31 is shown in FIG. 3-1 and the flower additives 6 is distributed in the supporting layer 32 without any matter added in the soft layer 31 is shown in FIG. 3-2. The distribution of tea additives 5 or flower additives 6 can be in any manner i.e. evenly or not evenly. The tea additives or the flower additives in the supporting layer 32 will last longer than if they are added in the memory foam. This is because memory foam is closer to the user and that bacteria tends to grow in memory foam due to the heat and perspiration absorbed from the user. The combination of heat and perspiration would have a negative effect on the tea additives or the flower additives. Tea additives or flower additives in the supporting layer 32 will have longer life time than tea additives or flower additives in the memory foam thus prolonging the service life of the regimen mattress.

Figure 4:
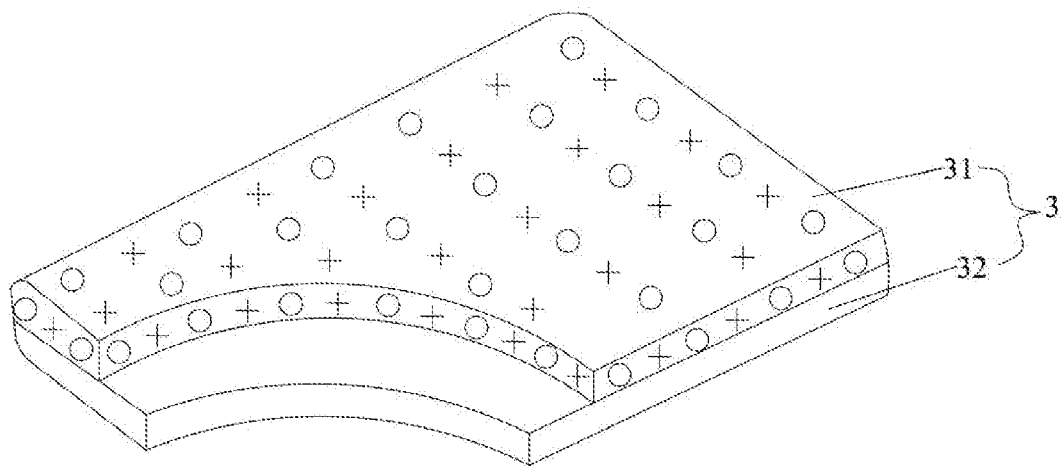
FIG. 4 is a schematic diagram of the HD foam according to a third embodiment of the invention with both tea additives and flower additives in the soft layer.

Referring to FIG. 4, a schematic diagram of the HD foam according to the third embodiment of present invention is shown. In the third embodiment, the tea additives 5 and the flower additives 6 are distributed in the soft layer 31 without any matter added in the supporting layer 32. The distribution of tea additives and flower additives can be in any manner i.e. evenly or not evenly. In addition to the above advantages of adding additives in the foam layer far away from the user, adding both the tea additives and the flower additives in the soft layer 31 will have both the advantages of the two additives. More preferably, the tea additives can mix with the flower additives in any proportion, the content of each additive is less than or equal to 0.5 wt %.

Figure 5:
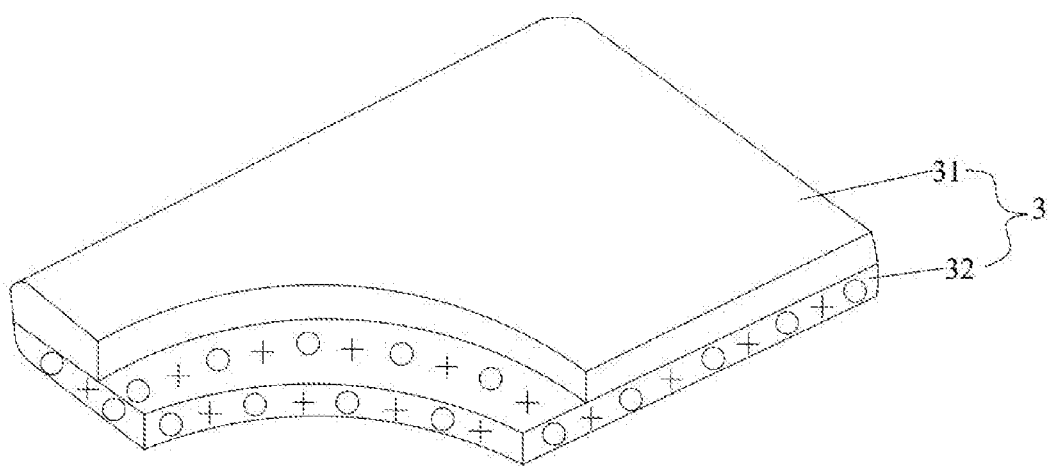
FIG. 5 is a schematic diagram of the HD foam according to a fourth embodiment of the invention with both tea additives and flower additives in the supporting layer.

Referring to FIG. 5, a schematic diagram of the HD foam according to the fourth embodiment of present invention is shown. In the fourth embodiment, the tea additives 5 and the flower additives 6 are distributed in the supporting layer 32 without any matter added in the soft layer 31. The distribution of tea additives and flower additives can be in any manner i.e. evenly or not evenly. In addition to the above advantages of adding additives in the foam layer far away from the user, adding both the tea additives and the flower additives in the supporting layer 32 will have both the advantages of the two additives. More preferably, the tea additives can mix with the flower additives in any proportion, the content of each additive is less than or equal to 0.5 wt %.

Figure 6:
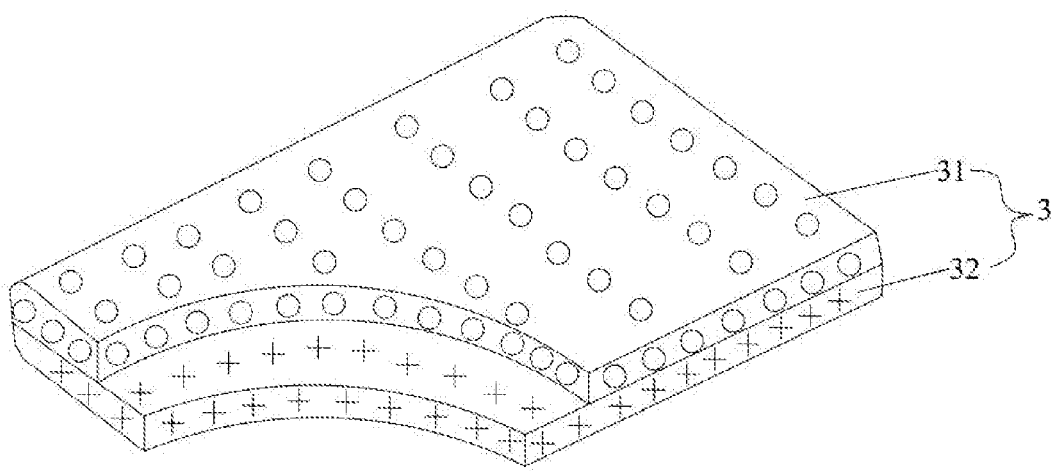
FIG. 6 is a schematic diagram of the HD foam according to a fifth embodiment of the invention with tea additives in the soft layer and flower additives in the supporting layer.

Referring to FIG. 6, a schematic diagram of the HD foam according to the fifth embodiment of present invention is shown. In the fifth embodiment, the tea additives 5 are distributed in the soft layer 31 and the flower additives 6 are distributed in the supporting layer 32. The distribution of tea additives and flower additives can be in any manner i.e. evenly or not evenly, the tea additives can mix with the flower additives in any proportion, the content of each additive is less than or equal to 0.5 wt %.

Figure 7:
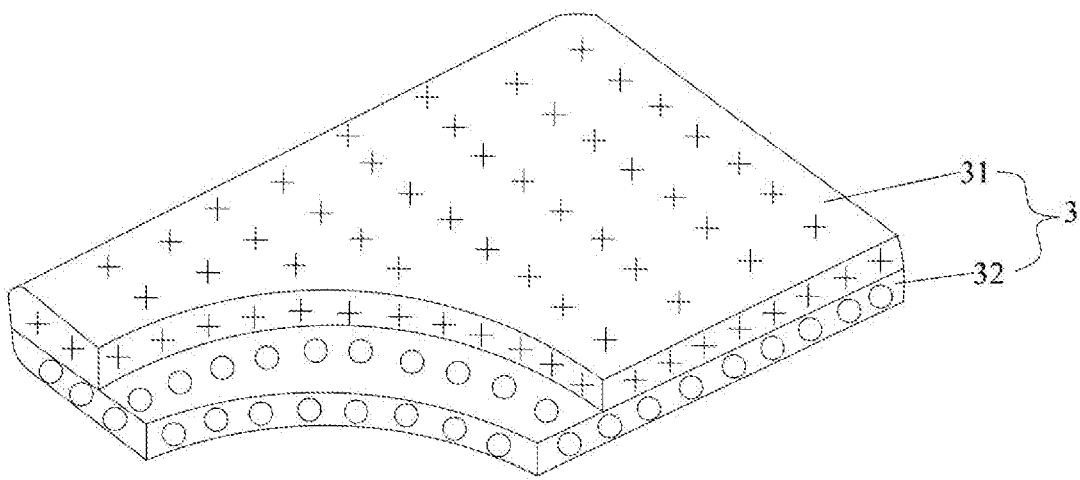
FIG. 7 is a schematic diagram of the HD foam according to a sixth embodiment of the invention with tea additives in the supporting layer and flower additives in the soft layer.

Referring to FIG. 7, a schematic diagram of the HD foam according to the sixth embodiment of present invention is shown. In the sixth embodiment, the tea additives 5 are distributed in the supporting layer 32 and the flower additives 6 are distributed in the soft layer 31. The distribution of tea additives and flower additives can be in any manner i.e. evenly or not evenly, the tea additives can mix with the flower additives in any proportion, the content of each additive is less than or equal to 0.5 wt %.

Figure 8:
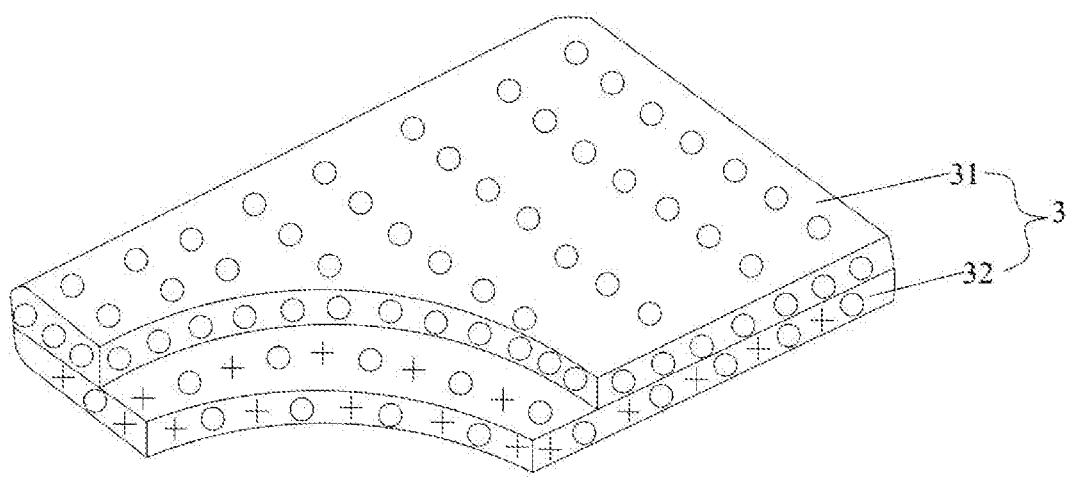
FIG. 8 is a schematic diagram of the HD foam according to a seventh embodiment of the invention with tea additives in the soft layer and mixture of tea additives and flower additives in the supporting layer.

Referring to FIG. 8, a schematic diagram of the HD foam according to the seventh embodiment of present invention is shown. In the seventh embodiment, the tea additives 5 are distributed in the soft layer 31, at the same time, the mixture of the tea additives 5 and the flower additives 6 are distributed in the supporting layer 32. The distribution of tea additives and flower additives can be in any manner i.e. evenly or not evenly, the tea additives can mix with the flower additives in any proportion, the content of each additive is less than or equal to 0.5 wt %.

Figure 9:
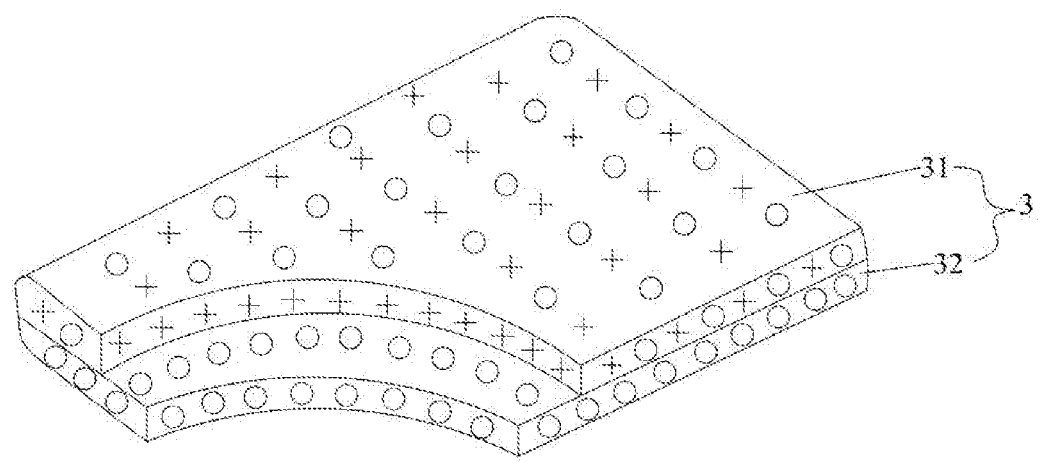
FIG. 9 is a schematic diagram of the HD foam according to an eighth embodiment of the invention with tea additives in the supporting layer and mixture of tea additives and flower additives in the soft layer.

Referring to FIG. 9, a schematic diagram of the HD foam according to the eighth embodiment of present invention is shown. In the eighth embodiment, the tea additives 5 are distributed in the supporting layer 32, at the same time, the mixture of the tea additives 5 and the flower additives 6 are distributed in the soft layer 31. The distribution of tea additives and flower additives can be in any manner i.e. evenly or not evenly, the tea additives can mix with the flower additives in any proportion, the content of each additive is less than or equal to 0.5 wt %.

Figure 10:
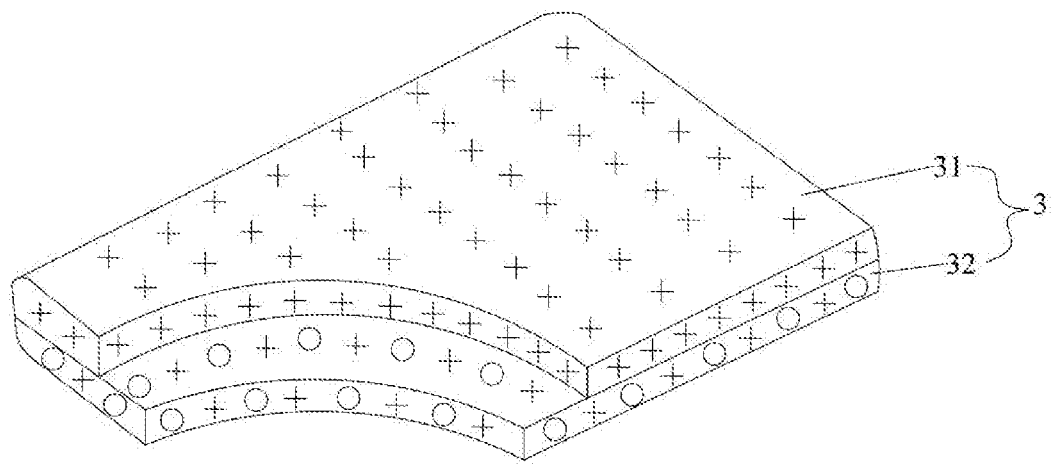
FIG. 10 is a schematic diagram of the HD foam according to a ninth embodiment of the invention with flower additives in the soft layer and mixture of tea additives and flower additives in the supporting layer.

Referring to FIG. 10, a schematic diagram of the HD foam according to the ninth embodiment of present invention is shown. In the ninth embodiment, the flower additives 6 are distributed in the soft layer 31, at the same time, the mixture of the tea additives 5 and the flower additives 6 are distributed in the supporting layer 32. The distribution of tea additives and flower additives can be in any manner i.e. evenly or not evenly, the tea additives can mix with the flower additives in any proportion, the content of each additive is less than or equal to 0.5 wt %.

Figure 11:
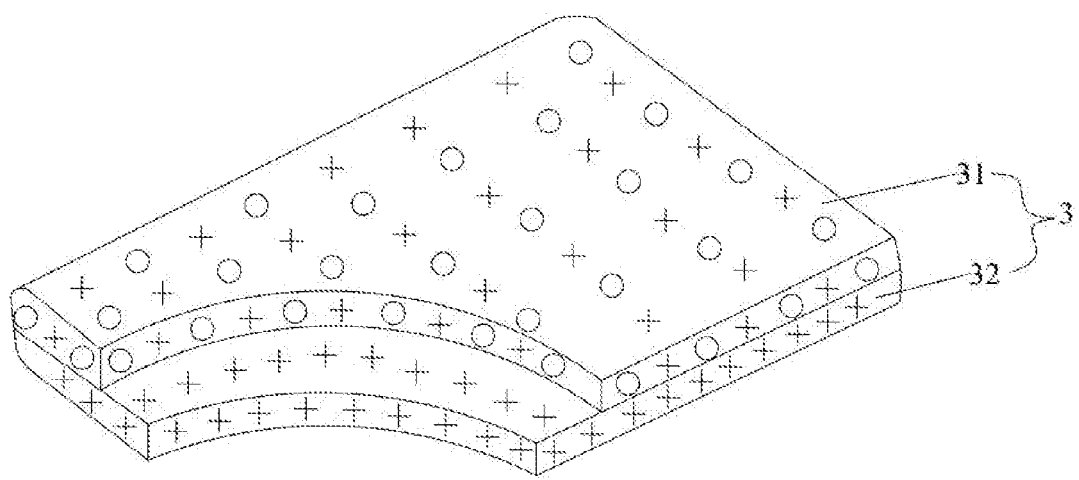
FIG. 11 is a schematic diagram of the HD foam according to a tenth embodiment of the invention with flower additives in the supporting layer and mixture of tea additives and flower additives in the soft layer.

Referring to FIG. 11, a schematic diagram of the HD foam according to the tenth embodiment of present invention is shown. The flower additives 6 are distributed in the supporting layer 32, at the same time, the mixture of the tea additives 5 and the flower additives 6 are distributed in the soft layer 31. The distribution of tea additives and flower additives can be in any manner i.e. evenly or not evenly, the tea additives can mix with the flower additives in any proportion, the content of each additive is less than or equal to 0.5 wt %.

In above listed embodiments, the HD foam 3 further includes the soft layer 31 and the supporting layer 32 disposed below the soft layer 31. The soft layer 31 is disposed, which not only enhances the comfortable feeling, making the user feel the mattress being softer, but also functions as a vibration absorber, reducing impulse when the user lies down. Soft layer 31 protects the supporting layer 32.

Figures 1, 12:
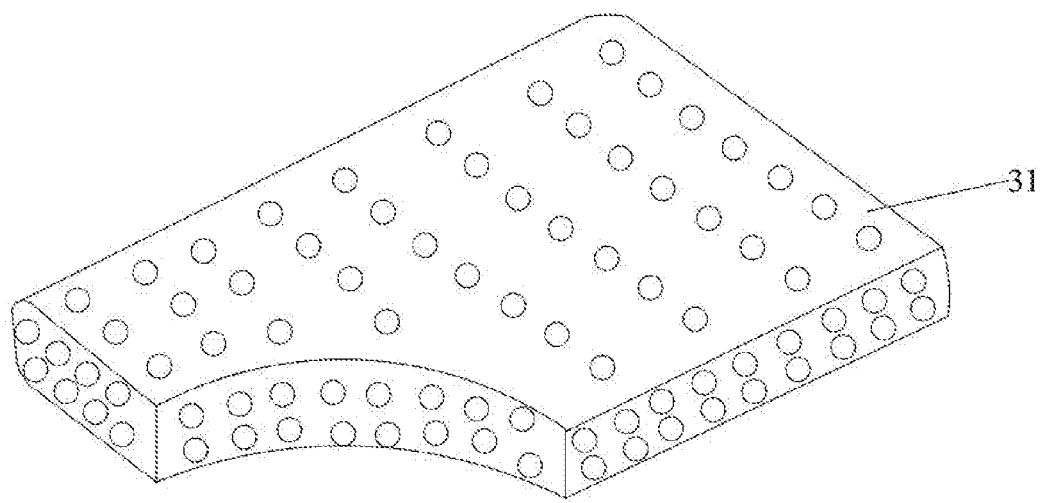
Figures 2, 12:
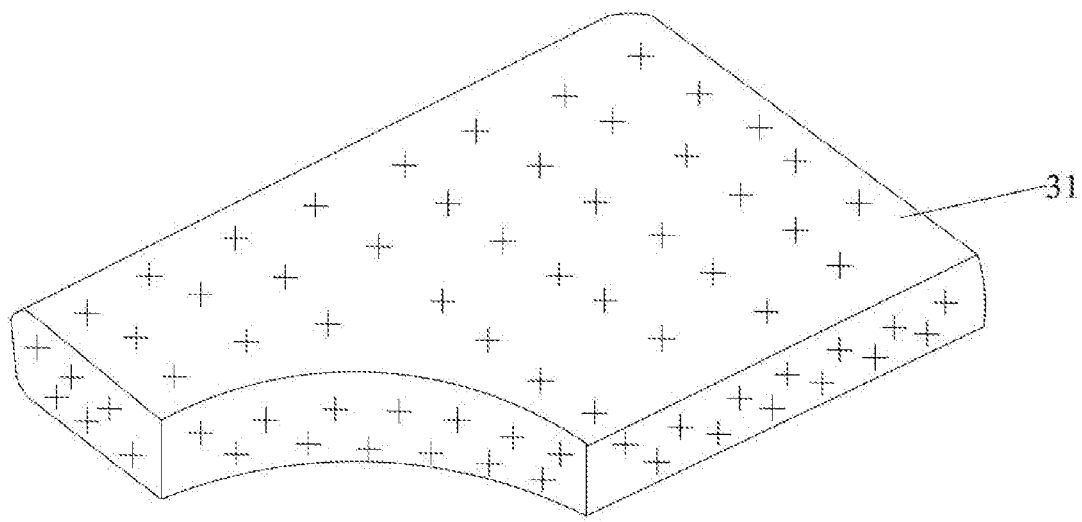

Referring to FIG. 12-1 and FIG. 12-2, schematic diagrams of the HD foam according to the eleventh embodiment of present invention respectively with tea additives and flower additives are shown. The tea additives 5 is distributed in the soft layer 31 is shown in FIG. 12-1 and the flower additives 6 is distributed in the soft layer 31 is shown in FIG. 12-2. The distribution of tea additives or flower additives can be in any manner i.e. evenly or not evenly.

Figure 13:
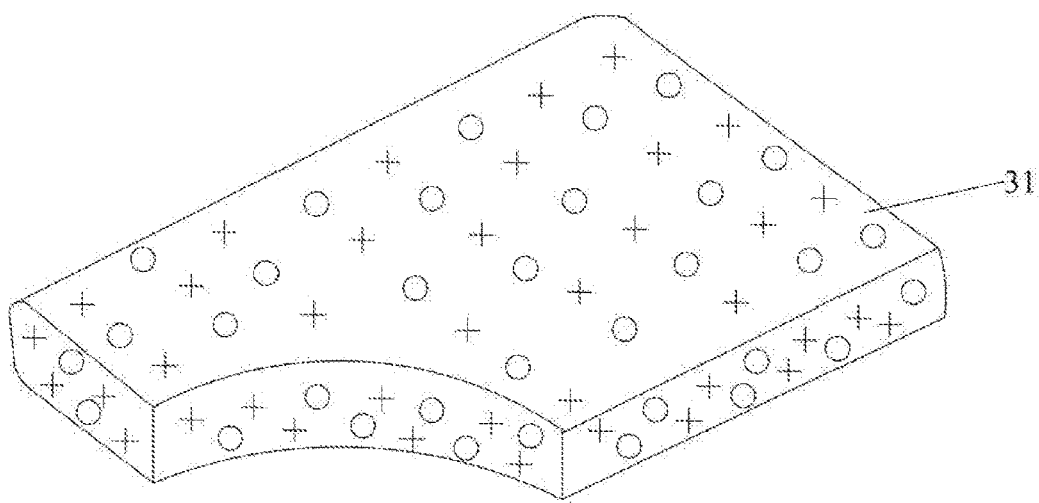
FIG. 13 is a schematic diagram of the HD foam according to a twelfth embodiment of the invention with both tea additives and flower additives.

Referring to FIG. 13, a schematic diagram of the HD foam according to the twelfth embodiment of present invention are shown. The tea additives 5 and the flower additives 6 are distributed in the soft layer 31. The distribution of tea additives or flower additives can be in any manner i.e. evenly or not evenly. The tea additives can mix with the flower additives in any proportion, the content of each additive is less than or equal to 0.5 wt %.

In the eleventh and twelfth embodiments, the HD foam 3 includes the soft layer 31 with no supporting layer 32. The soft layer 31 is disposed, which enhances the comfortable feeling, making the user feel the mattress being softer.

Figures 1, 14:
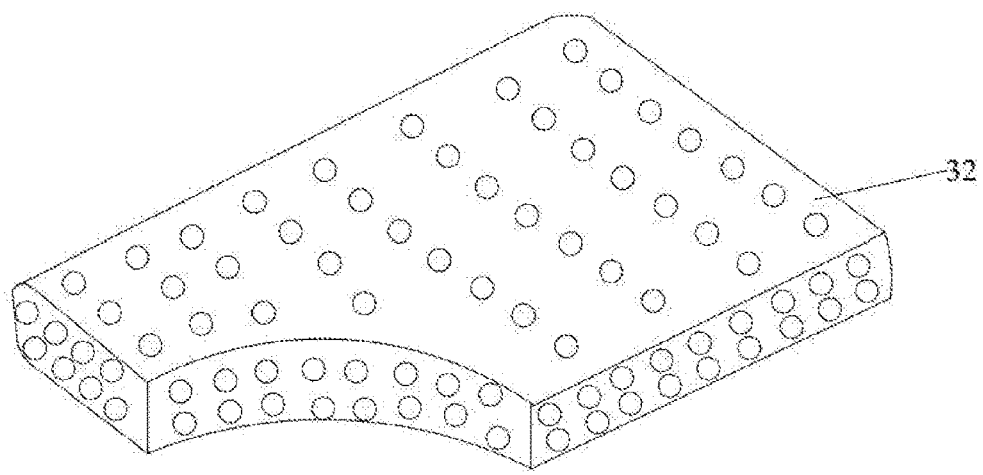
Figures 2, 14:
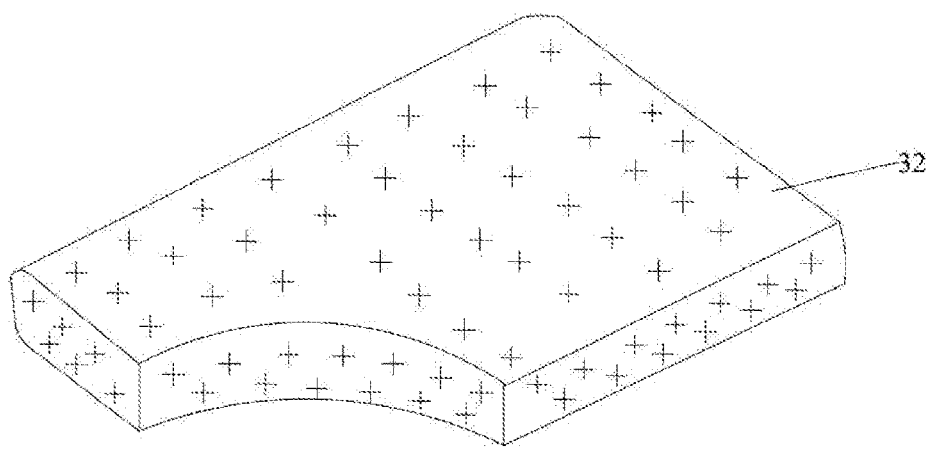

Referring to FIG. 14-1 and FIG. 14-2, schematic diagrams of the HD foam according to the thirteenth embodiment of present invention respectively with tea additives and flower additives are shown. The tea additives 5 is distributed in the supporting layer 32 is shown in FIG. 14-1 and the flower additives 6 is distributed in the supporting layer 32 is shown in FIG. 14-2. The distribution of tea additives or flower additives can be in any manner i.e. evenly or not evenly.

Figure 15:
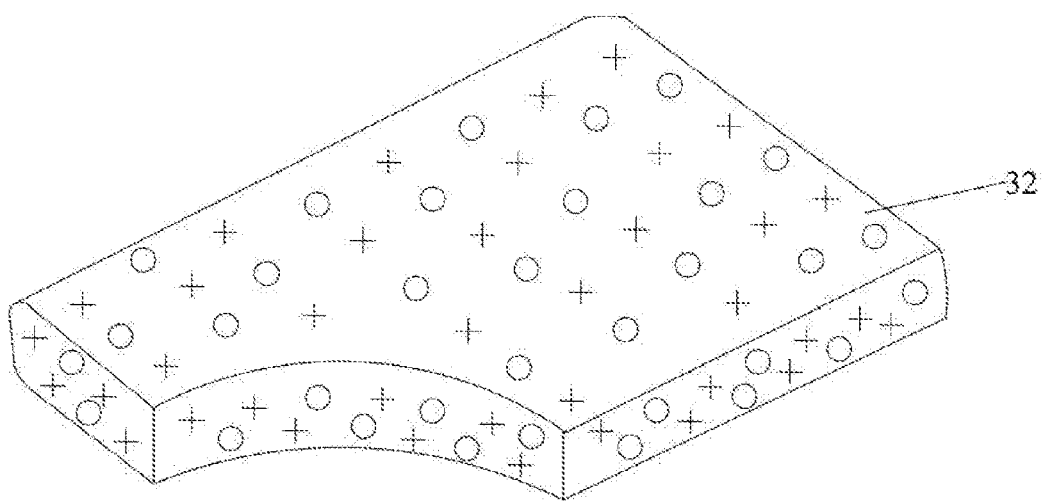
FIG. 15 is a schematic diagram of the HD foam according to a fourteenth embodiment of the invention with both tea additives and flower additives.

Referring to FIG. 15, a schematic diagram of the HD foam 3 according to the fourteenth embodiment of present invention are shown. The tea additives 5 and the flower additives 6 are distributed in the supporting layer 32. The distribution of tea additives or flower additives can be in any manner i.e. evenly or not evenly. The tea additives can mix with the flower additives in any proportion, the content of each additive is less than or equal to 0.5 wt %.

In the thirteenth and fourteenth embodiments, the HD foam 3 includes the supporting layer 32 with no soft layer 31. The supporting layer 32 is disposed, which functions as a vibration absorber, reducing impulse when the user lies down.

In the above embodiments of the invention, the HD foam 3 is made of 2,4-tolylene diisocyanate (TDI) and poly propylene glycol (PPG), the memory foam 2 is made of diphenyl-methane-diisocyanate (MDI) and poly propylene glycol (PPG). Other combinations of materials can be used as well.

The density of the supporting layer 32 is greater than that of the soft layer 31. The soft layer 31 and the supporting layer have a density ranging from 20D to 30D. More preferably, the soft layer 31 has a density ranging from 25D to 28D, and the supporting layer 32 has a density ranging from 27D to 30D.

The tea additives 5 are one or more selected from the group of green tea, black tea or white tea. The selection of various kinds of tea additives can achieve different effects. For example, the green tea has the advantages of radiation protection, fatigue elimination, promoting sleep, etc., which can prevent radiation from the electronic products used in the resting environment and make the user feel relaxed, thus leading to a comfortable sleep.

The flower additives 6 are one or more selected from the group of rose, jasmine, *Gardenia*, lilac, orchid, aloe or *Camellia*. The selection of various kinds of flower additives can achieve different effects. For example, the rose and jasmine has a bactericidal effect, the *Gardenia* and lilac can promote sleep, the orchid has a dusting effect, the aloe and *Camellia* can absorb harmful gas and purify air. Adding flower additives mentioned above is helpful to create a good resting environment, thus improving people's health condition.

Figure 16:
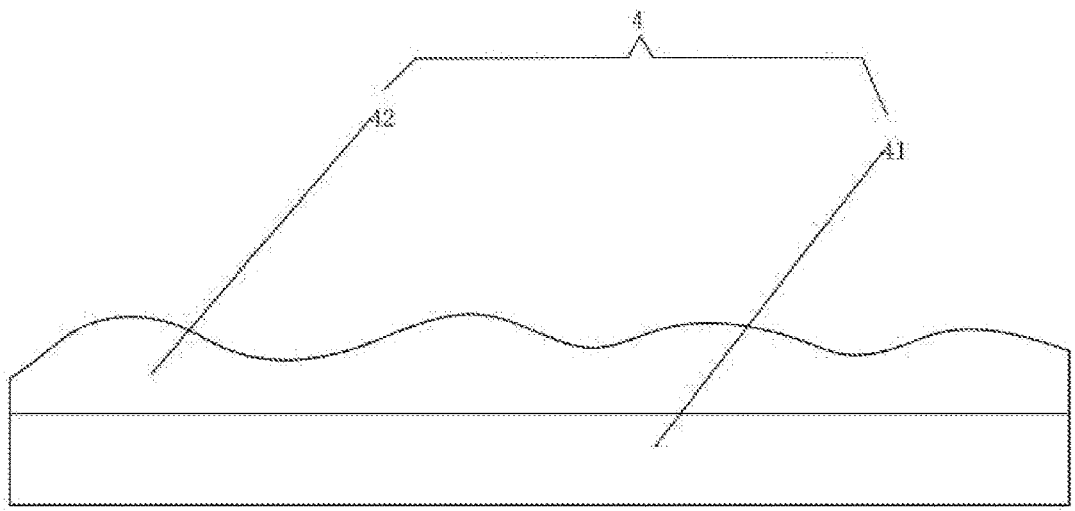
FIG. 16 is a section view of a two-layer structure of the cover in FIG. 1.

A section view of a two-layer structure of the cover is shown in FIG. 16. The cover 4 of all the above embodiments includes the inner cover 41 and the outer cover 42. The design of two covers, together with the selection of the materials, can achieve different functions of the mattress.

The inner cover 41 is a material selected from the group of fire retardant material or absorbing material. The use of fire retardant material for the inner cover 41 can ensure adequate security. While the use of absorbing material for the inner cover 41, such as the activated carbon, can effectively absorb bacteria and odor deposited in the memory foam 2 or the HD foam 3, thus keeping the mattress clean.

The outer cover 42 is a material selected from the group of waterproof breathable material, heat conduction material or friction heating material. The use of waterproof breathable material for the outer cover 42 is beneficial to the volatilization of the additives in the HD foam 3, making the additives spread to the air. The use of heat conduction material or friction heating material for the outer cover 42 makes the additives in the HD foam 3 easier to evaporate to the air due to the heat directly from the user or produced by the rubbing between the user and the outer cover 42 transfers to the HD foam to speed up the additives molecular motion.

The inner cover 41 and the outer cover 42 are detachable, which is convenient to clean and replace.

The cover 4 can be the inner cover 41, the outer cover 42, or both the inner cover 41 and the outer cover 42.

Figure 17:
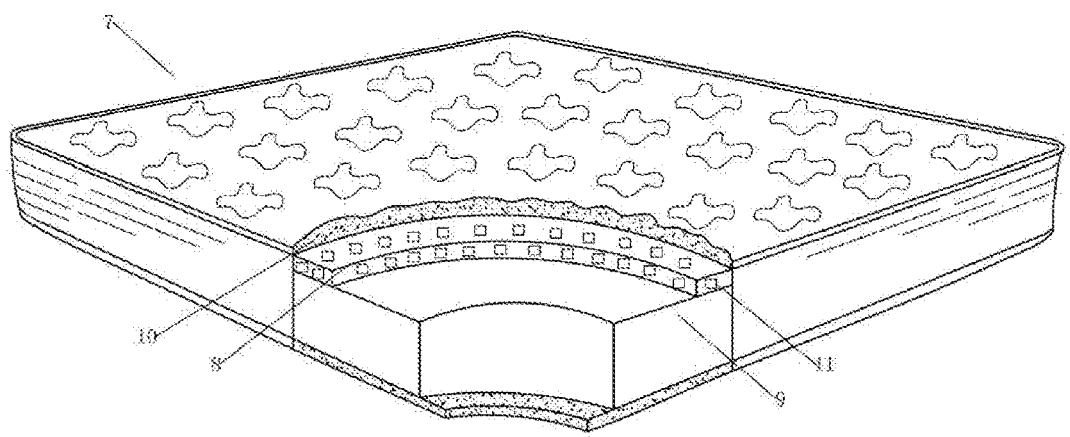
FIG. 17 is a schematic diagram of another regimen mattress of the present invention.

Another regimen mattress is shown in FIG. 17. The regimen mattress 7 includes the memory foam 8, the high density (HD) foam 9 below the memory foam 8, and the cover 10 covering the memory foam 8 and the HD foam 9 together to form the entire mattress 7. The memory foam 8 contains the first functional additive. The first functional additive 11 is any matter that has the effects of degerming and deodorization. The HD foam 9 can contain no additive or be any one of the above embodiments.

The density of the memory foam 8 is greater than a density of the HD foam, preferably, the memory foam 8 has a density ranging from 40D to 60D, more preferably, the memory foam 8 has a density ranging from 40D to 42D.

The first functional additive is a tea additive or a flower additive, preferably, the tea additive is one or more selected from the group of black tea or white tea, the flower additive is one or more selected from the group of rose, jasmine, *Gardenia*, lilac, orchid, aloe or *Camellia*.

The foregoing descriptions are merely preferred embodiments of the present invention, and are not used to limit the scope of the present invention. Any modifications, equivalent replacements and improvements made within the spirit and principle of the present invention should be included in the protection scope of the present invention.

I claim:

1. A regimen mattress comprising: a memory foam, a high density (HD) foam below the memory foam, and a cover covering the memory foam and the HD foam together to form an entire mattress; wherein a functional additive comprising a tea additive or a flower additive or both tea additive and flower additive contained only in the HD foam, the HD foam comprises a soft layer and a supporting layer disposed below the soft layer; wherein the density of the supporting layer is greater than a density of the soft layer.

2. The regimen mattress of claim 1, wherein the cover comprises an inner cover and an outer cover.

3. The regimen mattress of claim 2, wherein the inner cover is made of a material selected from the group consisting of a fire retardant material and an absorbing material.

4. The regimen mattress of claim 2, wherein the outer cover is made of a material selected from the group consisting of a waterproof breathable material, a heat conduction material and a friction heating material.

5. The regimen mattress of claim 2, wherein the inner cover and the outer cover are detachable.

6. The regimen mattress of claim 1, wherein the at least one of the tea additive or the flower additive contained in the HD foam is not evenly distributed.

7. The regimen mattress of claim 1, wherein the functional additive comprises the flower additive.

8. The regimen mattress of claim 7, wherein the flower additive comprises at least one of lilac or orchid.

9. The regimen mattress of claim 1, wherein the functional additive is located in the soft layer but not in the supporting layer.

10. The regimen mattress of claim 1, wherein the tea additive is located in the soft layer but not in the supporting layer.

11. The regimen mattress of claim 1, wherein the flower additive is located in the soft layer but not in the supporting layer.

12. The regimen mattress of claim 1, wherein the tea additive is located in the supporting layer but not in the soft layer.

13. The regimen mattress of claim 1, wherein the flower additive is located in the supporting layer but not in the soft layer.

14. The regimen mattress of claim 1, wherein the functional additive is located in the supporting layer but not in the soft layer.

15. The regimen mattress of claim 1, wherein the tea additive is located in the soft layer and the flower additive is located in the supporting layer.

16. The regimen mattress of claim 1, wherein the flower additive is located in the soft layer and the tea additive is located in the supporting layer.

17. The regimen mattress of claim 1, wherein the tea additive is located in the soft layer, and the tea additive and the flower additive are located in the supporting layer.

18. The regimen mattress of claim 1, wherein the HD foam is made from 2,4-tolylene diisocyanate (TDI) and poly propylene glycol (PPG).

19. The regimen mattress of claim 1, wherein the memory foam is made from diphenyl-methane-diisocyanate (MDI) and poly propylene glycol (PPG).

20. The regimen mattress of claim 1, wherein the tea additive comprises at least one of black tea and white tea, and wherein the flower additive comprises at least one of rose, jasmine, *gardenia*, lilac, orchid and aloe.

21. A regimen mattress comprising: a memory foam, a high density (HD) foam below the memory foam, and a cover covering the memory foam and the HD foam together to form an entire mattress; wherein a functional additive comprising at least one of a tea additive or a flower additive is only contained in the HD foam, the HD foam is made from 2,4-tolylene diisocyanate (TDI) and poly propylene glycol (PPG), the memory foam is made from diphenyl-methane-diisocyanate (MDI) and poly propylene glycol (PPG), the tea additive comprises at least one of black tea and white tea, and wherein the flower additive comprises at least one of rose, jasmine, *gardenia*, lilac, orchid and aloe, the HD foam comprises a soft layer and a supporting layer disposed below the soft layer, and the soft layer has a density ranging from 25D to 28D, the supporting layer has a density ranging from 29D to 30D, and the memory foam has a density ranging from 40D to 42D.

22. A regimen mattress comprising: a memory foam, a high density (HD) foam below the memory foam, and a cover covering the memory foam and the HD foam together to form an entire mattress; wherein a functional additive comprising at least one of a tea additive or a flower additive is only contained in the HD foam, the HD foam is made from 2,4-tolylene diisocyanate (TDI) and poly propylene glycol (PPG), the memory foam is made from diphenyl-methane-diisocyanate (MDI) and poly propylene glycol (PPG), the tea additive comprises at least one of black tea and white tea, and wherein the flower additive comprises at least one of rose, jasmine, *gardenia*, lilac, orchid and aloe, and the HD foam comprises a soft layer and a supporting layer disposed below the soft layer; the soft layer has a density ranging from 25D to 28D, the supporting layer has a density ranging from 29D to 30D, and the memory foam has a density ranging from 40D to 42D.

* * * * *